United States Patent [19]

San Miguel

[11] 4,379,401
[45] Apr. 12, 1983

[54] SYSTEM FOR MEASURING PLATE DEFORMATION PRODUCED BY EXPLOSIVE SHOCK WAVES, AND MOTION-SENSING ACCELEROMETER TRANSDUCER USED THEREIN

[75] Inventor: Anthony San Miguel, Leucadia, Calif.

[73] Assignee: The United States of America as represented by the Secretary of the Army, Washington, D.C.

[21] Appl. No.: 297,294

[22] Filed: Aug. 28, 1981

[51] Int. Cl.³ .................... G01N 33/20; G01N 33/22; G01N 3/30
[52] U.S. Cl. ............................................. 73/12; 73/35
[58] Field of Search ................. 73/35, 12, 862.53, 492

[56] References Cited

U.S. PATENT DOCUMENTS

| 2,761,309 | 9/1956 | Pearson et al. | 73/12 |
| 3,389,606 | 6/1968 | Watson | 73/35 X |
| 3,395,569 | 8/1968 | Sheridan et al. | 73/35 |

Primary Examiner—James J. Gill
Attorney, Agent, or Firm—Peter A. Taucher; John E. Becker; Nathan Edelberg

[57] ABSTRACT

A novel testing system utilizing a novel subcombination multiple pin/probe type, motion-sensing accelerometer transducer, capable of sensing exceptionally high levels of structural motion, in the domain of from about 1,000,000 to 10,000,000 Gs (force of gravity). Such motion may be imparted by shock wave forces generated by detonation of high energy ballistic and/or land mine charges, thereby generally deforming some portions of closely adjacent, high strength structures such as steel armor plate being tested. This novel accelerometer transducer comprises at least two and preferably from six to eight potentially deformable pin-like contact probes preferably of pure annealed metal which preferably project from both sides of a support fixture. One set of contact pin ends are generally spaced at slightly different distances from an adjacent surface to be tested. The other ends of said pin probes are connected respectively to parallel subcircuits each having a series connected resistance capacitor and oscilloscope. The parallel subcircuits are connected further with a principal circuit having an on-off power source, and then to the negative ground formed by the rigid armor test plate structure. When the power source is "on", pin-plate contact resulting from such blast deformation force progressively energizes the respective subcircuits, from which the timed differences between contacts and other data are measured and used primarily to novelly compute instantaneous velocity and average acceleration of such deformation.

17 Claims, 19 Drawing Figures

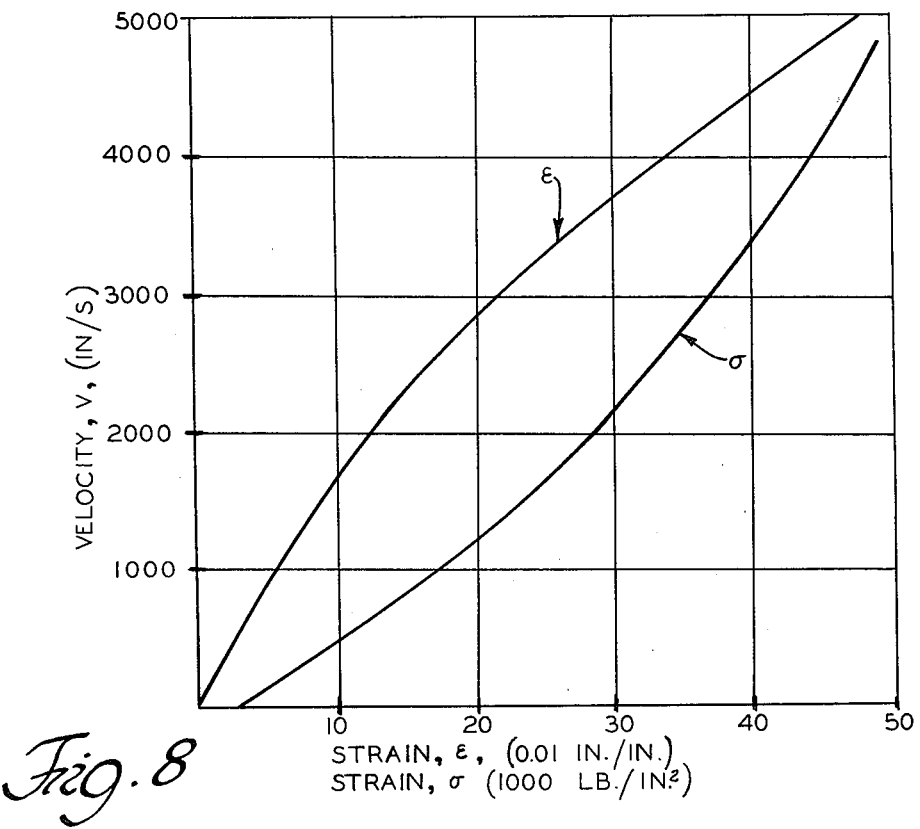
Fig. 8 CALCULATED VALUES OF PARTICLE VELOCITY V AS A FUNCTION OF STRAIN AND STRESS FOR PURE ANNEALED COPPER
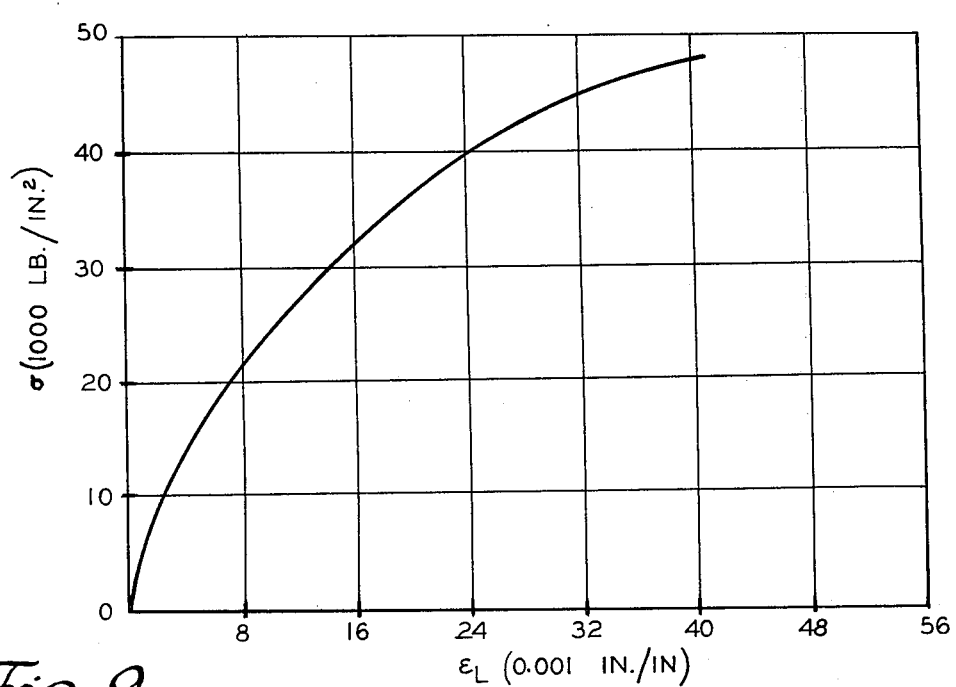
Fig. 9 INITIAL PORTION OF STRESS-STRAIN RELATIONSHIP IN COMPRESSION FOR PURE ANNEALED COPPER

SYSTEM FOR MEASURING PLATE DEFORMATION PRODUCED BY EXPLOSIVE SHOCK WAVES, AND MOTION-SENSING ACCELEROMETER TRANSDUCER USED THEREIN

GOVERNMENT INTEREST

The invention described herein may be manufactured, used, and licensed by or for the Government for governmental purposes without payment to me of any royalty thereon.

BACKGROUND AND SUMMARY OF THE INVENTION

The present invention relates to a novel blast effect test accelerometer transducer and to a novel method of use thereof to ascertain among other things, instantaneous velocity of surfaces subjected to sudden acceleration and/or the amount of deflection of armor plate when subjected to explosive blast forces. Unlike any such prior art motion-sensing accelerometer transducers of which I am aware, this novel accelerometer device is capable of withstanding and measuring exceptionally high levels of structural motion, i.e., in the domain of from about 1,000,000 to 10,000,000 Gs. This enables measurement for the first known time of deformation of steel armor plate when subjected to high energy explosive blasts, such as land mines.

Scaled model tests have long been the basis for military tank floor studies because of both safety considerations and the complexity of blast-structure interaction phenomena. The objective for scale testing is to obtain quantitative data for prototype design, to identify significant design variables, to estimate the extreme performance potential of an existing prototype system, and to investigate new phenomena when there are no alternatives. It should be noted that reduced scale testing for metallic plate plastic deformation response can only be presumed to be an accurate representation of prototype plastic deformation response if the true full scale plastic failure criteria is invariant; however, such is not the case for all materials in general. Strain rate effects and related yield phenomena cannot be accurately scaled. The general design rule of thumb is that any such model tests are to be interpreted in terms of deformation, and that prototype tests be used to obtain failure criteria. Therefore, when testing relative to military tanks or similar armored vehicles whose floor armor is subjected to mine blasts or the like, the degree of plate displacement is the important measurement in such tests. Thus, in such tests, the corresponding displacement of a tank floor plate is deemed to be characterized by a step increase in force attendant an accompanying step increase in acceleration thereby producing useful data including a continuous time history of velocity and related time displacement.

Most types of prior art motion-sensing transducer accelerometers designed to sense velocity and displacement of which I am aware are not suitable for use in scaled dynamic test models of the type being discussed herein. Examples of known force and motion-sensing transducers are the quartz sensors or transducers manufactured by PCB Piezotronics, a company located in Buffalo, N.Y. 14225. Other piezoelectric and piezo resistant type accelerometers are available from a company named ENDEVCO. Some of the prior art's unsuitability is attributed to both an inability to withstand and measure the above-stated exceptionally high force levels (1,000,000–10,000,000 Gs) as by breakage of the quartz sensor leads or probes, and also the requirement that relatively large weight masses be attached to the test model therefore seriously affecting the inertial properties of the armor system being tested.

The novel testing method in essence utilizes an explosive charge customarily of generally disc geometry having diameter d and thickness a (FIG. 5) which is placed a given distance, R, from the bottom of the test plate. Upon detonation, a time expedant pressure is applied to the test plate resulting in a positive impulse, designated by the symbol I, which is bounded by time t. Using well known scaling relationship and the Hopkinson blast wave scaling law, in conjunction with one-quarter ($\frac{1}{4}$) scale tests, i.e., physical scaling factor $\lambda = \frac{1}{4}$, the scaled model parameters are obtained. In this regard reference is made to the publications "*Explosions In Air*" by W. E. Baker, University of Texas Press, Austin, Tex., 1973; and also to D. J. Schuring's "Scale Models in Engineering," *Pergamon Press*, New York, 1977, and W. E. Baker et al. "Similarity Methods in Engineering Dynamics, Theory and Practice of Scale Modeling," Hayden, Rochelle Park, N.J., 1973. Although the use of the Hopkinson blast law at close standoff distance could lead to misleading results since the expansion and shock waves of the blast diffuse or decay at different rates which are not subject to scaling, sufficient experimental evidence exists to indicate that the law is a reasonable approximation of the events which occur during the explosion. In this regard, reference may be made to a publication authored by Wenzel, A. B. and Esparza, E. D., entitled "Measurements of Pressures and Impulses at Close Distances from Explosive Charges Buried and in the Air," Army Mobility Equipment Research and Development Center, TR SwRI02-31231, August 1972. Also, the time scale impulse and plate response must be interpreted in a homologous manner. It must be emphasized that the scaling used in this method assumes that viscosity, strain rate, gravity, and other nonlinear thermoviscoelastic phenomena can be neglected.

Scaled model response data exhibits wide scatter. For this reason, the fixity of the model test plate should approach classical clamped conditions; that is, the boundaries of the test plate should be relatively fixed in space so that both shear moments must be readily reacted by the holding fixture; and the holding fixture also should be representative of the full scale apparatus being tested. For example, in the instant case, the scale should approach the ratio exhibited by the tank vehicle to its belly armor, i.e., a 28:1 hold-down weight ratio of the test plate fixture to test plate. The overall length of the test fixture was 6 ft (183 cm), its width was 31 inches (78.7 cm); and the model tank floor plate measured 2 ft (61 cm) by 2 ft (61 cm), having an area 15" (38 cm) by 15" (38 cm) exposed to react to the blast load. When the displacement of the plate occurs, the surface of the plate is temporarily deformed and forced into contact with the pins of the accelerometer transducer, thereby generating transient plate deformation data.

The accelerometer transducer is comprised of at least two, and preferably of six to eight pure annealed copper pin-type probes which are housed in a rigid collar flange and body block on a support fixture so that the pins project downwardly as shown at different lengths. Each probe is operatively connected in an initially open circuit manner in series with a resistance capacitor and an oscilloscope or other suitable fast recording means. These plurality pin probe circuits are in parallel connected with an electrical power source via an "on-off" switch and also collectively with a negative ground point on said test plate. When the deformation of the plate occurs while being subjected to a blast force, each physical contact by a copper pin with the upper surface progressively closes or activates the respective circuits and thereby discharges its circuit's single channel discharge capacitor with the resulting signal being recorded on the oscilloscope or other recording means, and also preferably on a tape recorder. The recorder is used to record the acoustical equivalent of the electrical signal produced on the oscilloscope.

In this manner the electrically measured time of arrival of the test plate surface is obtained. Since the relative distance of the end of each of the pin probes from the test surface is measured prior to blast detonation (these distances being represented by $\Delta x$), the average velocity may be obtained by adding together the relative velocity as measured at each of the pins and dividing that number by the number of pin probes used in the test. The average velocity for each plate tested is obtained by dividing the known distances ($\Delta x$) between the ends of the pins and the plate surface by the time increments between contacts. The time from detonation ignition of the blast explosive to plate-to-pin contact is obtainable from photographic prints of signal sweep traces on the respective oscilloscopes. By subtracting the time between pin or probe contacts, the incremental times (designated $\Delta t$) are obtainable. The average velocity of the plate surface is then computable from $((\Delta x)/\Delta t)$ and thus assumed to occur at $((\Delta t)/2)$. In addition, instantaneous velocity measurements at the time of respective pin contact can be determined from engineering graphs to obtain the stress intensity-plastic deformations of a given rod relationship for different known rod materials, as the basis for a velocity measuring transducer. By assuming initial incompressible flow for the copper pin at the time of the test surface-to-pin probe contact, the instantaneous velocity at that time can be obtained by measuring the pin probe diameter at the end which contacts the test surface both before and after the test is concluded, and using known velocity longitudinal strain relationships. Thus, the time of arrival of the test surface to each pin probe enables the calculation of average acceleration of the test plate surface.

BRIEF DESCRIPTION OF THE DRAWINGS

FIGS. 5A through 5F depict a series of end elevational views representing the progressive events which occur during testing, wherein;

FIG. 5B shows the land mine detonator igniting and the commencement of explosive force action;

FIG. 5C shows the explosive force as it is about to contact the test plate;

FIG. 5D shows the explosive force being transmitted to the test plate with the resulting initial deformation;

FIG. 5E depicts the progressively increasing deformation of the test plate as well as the mine explosion debris;

FIG. 5F depicts the return of the test plate to approximately its original configuration;

FIGS. 8 and 9 are engineering graphs evolved from previous research studies from which instantaneous velocity of contact can be predicted (from FIG. 8), when knowing or given in tensile-stress relationship for annealed pure copper materials (from FIG. 9).

DETAILED DESCRIPTION OF A PREFERRED EMBODIMENT

Figure 1:
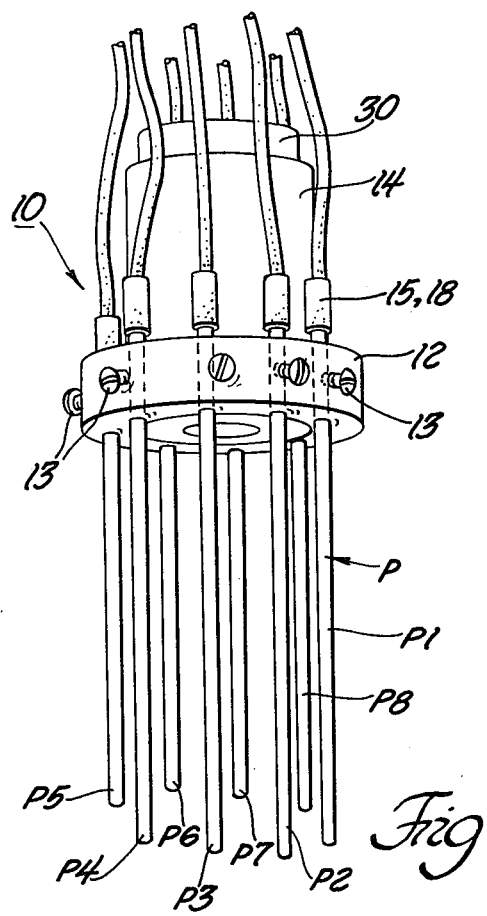
FIG. 1 depicts an elevational view partially in perspective of the novel accelerometer transducer hereof before being subjected to any force loading by plate deformation.
Figure 2:
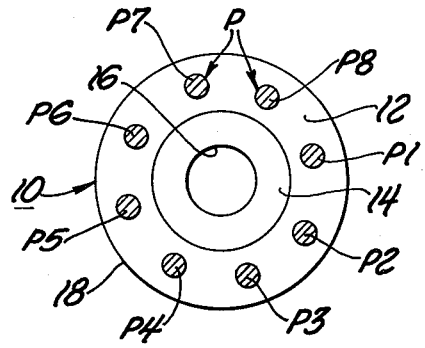
FIG. 2 is a bottom end view of the accelerometer transducer of FIG. 1.
Figure 3:
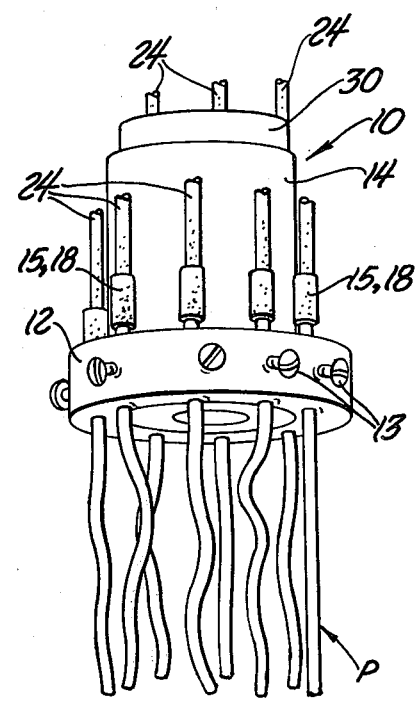
FIG. 3 is a perspective view similar to FIG. 1, but showing the approximate pin deformation after force loading by test plate deformation.

Referring now to the drawings and more particularly to FIGS. 1 through 3, the novel blast accelerometer transducer (minus its timing means) is generally designated 10 and preferably comprises a plurality of eight pure, annealed copper pins P supported as probes in a rigid material collar or flange 12. It should be noted that other relatively soft, pure metal such as aluminum, silver, gold, and lead can be also used as the pin probes. The probes must be of pure annealed material to assure reliable repeatability of test results. Otherwise results would reflect undesirable scatter due to different alloy constituents.

The collar 12 preferably is made integral with a body block 14, or otherwise is unitarily joined therewith in a suitable manner. Collar or flange 12 is provided with a series of peripheral holes or notches through which the pin probes pass and are held in their respective different length places, as by set screws 13 or other suitable restraining means. If the body block or collar are metallic, the pins are to be electrically insulated therefrom as by a varnish or other dielectric coating or bushing (not shown). The probe pins P are respectively designated P1, P2, P3, P4, P5, P6, P7, and P8. Attached to the pins are electrical conductor wires W1 through W8, one for each pin. Each wire via fastening means 15 is connected to its respective pin in circuit with a separate resistance capacitor and oscilloscope, to be described hereinafter. The body block 14 may be optionally provided with an opening 16 preferably through its center. The purpose of the opening 16 is to optionally accommodate the easy passage of a rigid calibrated measuring rod 20 (not shown), if desired to be used. Block 14 has an upper portion 30 adapted to fixedly mount within a hole 28 preferably in the midpoint of transverse middle beam 38 of the test frame 24. If a measuring rod is used, it is perpendicular to both the said transverse member 38 of the test frame 24 and to the major plane of a selected rigid test plate 32. Such a rod would be equipped with surface calibrations such as to enable one to compute the upward movement of such a rod as it relates to test plate deformation.

Again referring to the pins P, they are shown arranged generally in order of decreasing length in a circular pattern around the aforementioned collar 12. It must be noted that neither the support collar nor the arrangement of the pins need be circular. Other possible pin arrangements include linear, square, triangular, etc., and the length arrangement of the pins does not have to be in any particular order so long as they all are of somewhat different lengths. The longest pin or that projecting the farthest will naturally be the first to be contacted by the deforming plate, and the last to be contacted will naturally be the one of shortest length or projection. They are essentially arranged from shortest to longest merely for convenience, and not of necessity. The pins are preferably disposed perpendicular to the major plane of the collar 12 and, in turn, are mounted also perpendicular to the surface of the test plate 32.

Figure 7:
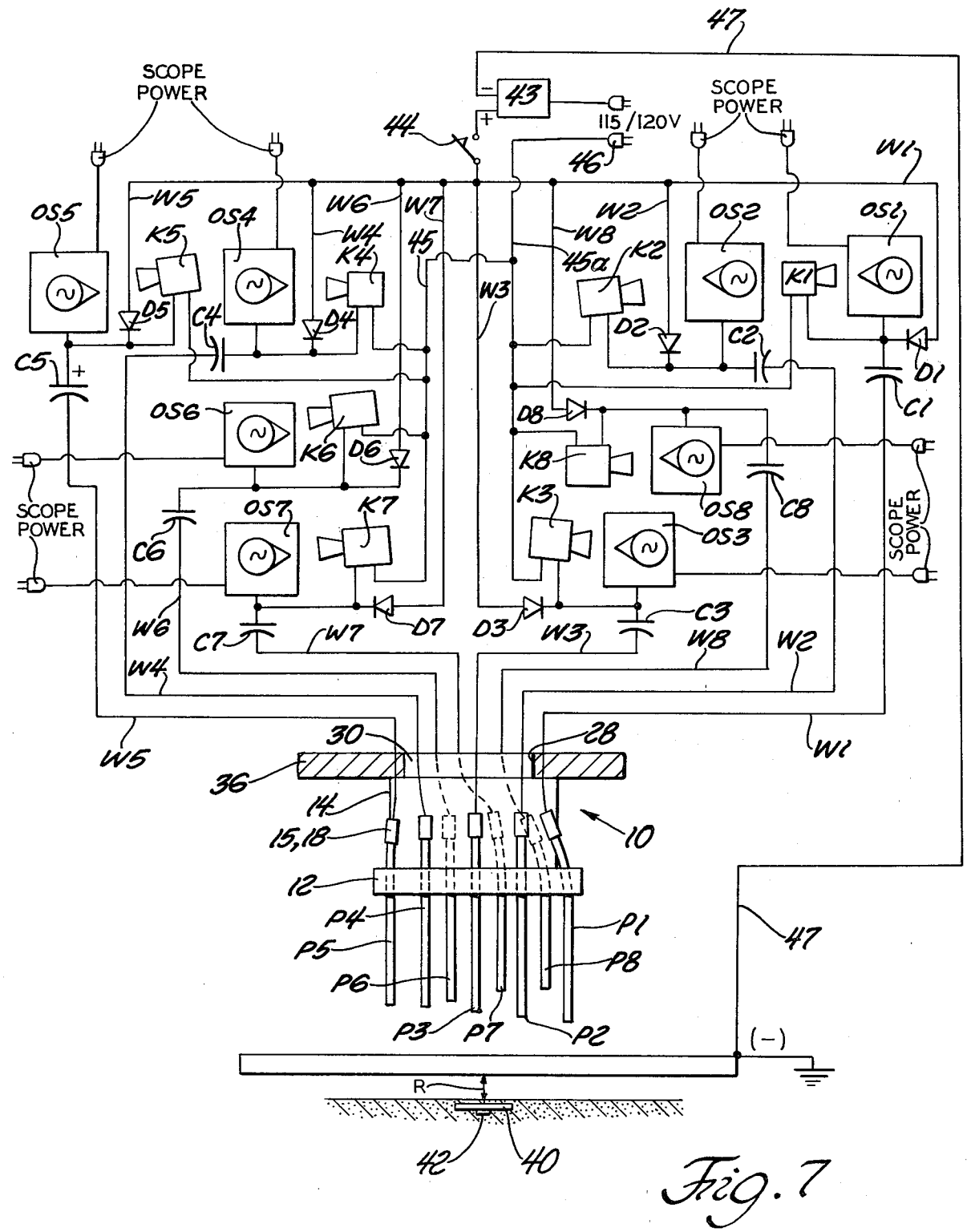
FIG. 7 depicts the blast accelerometer transducer in conjunction with an exemplary electrical schematic wiring diagram embodying respective capacitors and oscilloscopes and a power source, in one preferred mode of operation.

The FIG. 7 electrical wiring diagram in conjunction with a schematic of the blast accelerometer 10 exemplifies one manner of electrically recording the degree of test plate deformation from which to compute the average acceleration thereof. Each copper pin or probe P is connected by means of corresponding conductor wire W to a single discharge resistance capacitor, each of which is designated C1 through C8 respectively. Wire connections to the respective upper ends of each pin via the aforesaid means 15 may be permanent, as by soldering, or they may be by any suitable easy disconnect friction clip-on means with protective sleeve subassemblies, generally depicted 18, as part of an overall principal circuit.

Each capacitor is connected in series to a suitable fast response timing device such as an oscilloscope designated OS-1 through OS-8 respectively. If the oscilloscopes are not of the memory type, then each in turn is connected to a suitable camera or other means for making a recording of the oscilloscope readings. The respective capacitors are charged preferably from a conventional line power unit 43, via "on-off" switch 44 associated therewith. The camera recording means contemplated herein are preferably high speed cameras K1-K8, each capable of taking a picture of the respective scope's tracing at the instant the respective circuits are closed by contact of the pins with the deforming test plate. Each camera utilized is appropriately connected in the principal circuit and also via lines 45 and 45a with a suitable power source via line plug 46. As illustrated, the positive side of the power source 43 is appropriately connected via said on-off switch means 44 to the aforesaid components, and the negative side is ultimately connected via line 47 with the test plate 32 to be tested, as the negative ground. It should be noted that the system alternatively could be wired for positive ground, if so desired. The respective oscilloscopes are connected to a suitable power source via line connectors and plugs as per legends "scope power" in FIG. 7. The subcircuit wires W1-W8 are preferably provided with suitable diode means D1-D8, or the like, to better assure transfer of the capacitor discharge pulse signal over to the respective shutter trip functions of the respective cameras. When each pin probe is contacted progressively by the deforming test surface, an electrical circuit via its discharge capacitor is completed and the corresponding oscilloscope and camera are simultaneously activated. It is preferable to use an RC (resistance capacitor) circuit utilizing single discharge capacitors with a monitoring oscilloscope for each pin circuit. Thus, when the plate-to-pin contact is made, the capacitor's discharge signal is instantly picked up by and displayed on the oscilloscope by the time sweep spikes. The cameras can record these different time sweep spikes, i.e., from detonation to contact, during use of the system. By using the record of two such sweep spikes for each pin, the difference in time between the various contacts can be obtained. The respective contact signals of the single channel capacitors also my be recorded on a tape recorder.

It should be noted in passing that because oscilloscopes are now available with memory capable of recording the tracing produced and of subsequently reproducing that recording when desired, the use of the high speed camera is perhaps unnecessary when using an oscilloscope of this nature. Each pin and its associated conductor wire W1-W8, together with the series connected capacitor and oscilloscope of each, constitute separate in-parallel subcircuits within the overall principal circuit. Because each completed plate-pin contact creates a different trace on its corresponding oscilloscope, from a comparison of all the tracings thus obtained, it is possible to electrically measure the arrival of the deforming surface of plate 32 to the copper pins P, and to then compute the difference in time from the contact of the first pin to the successive contacts for any and/or all of the other pins.

Figure 4:
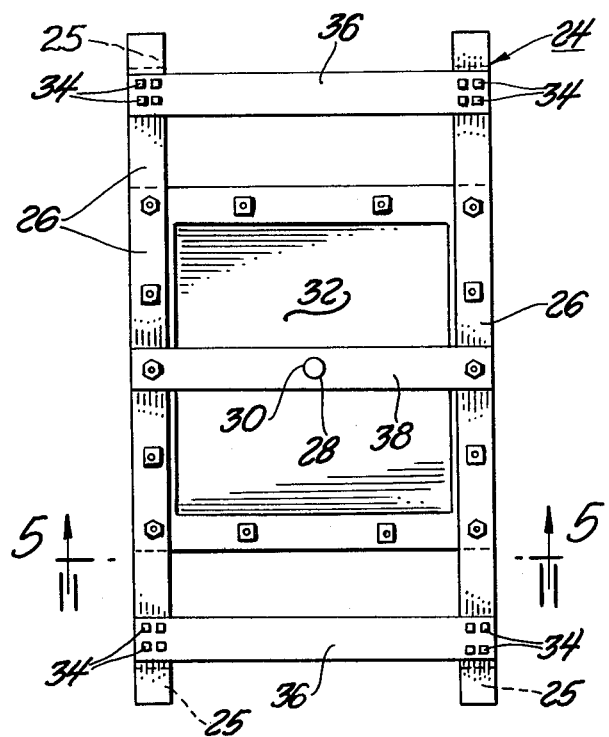
FIG. 4 is a top plan view of the support frame holding a test plate.
Figure 5:
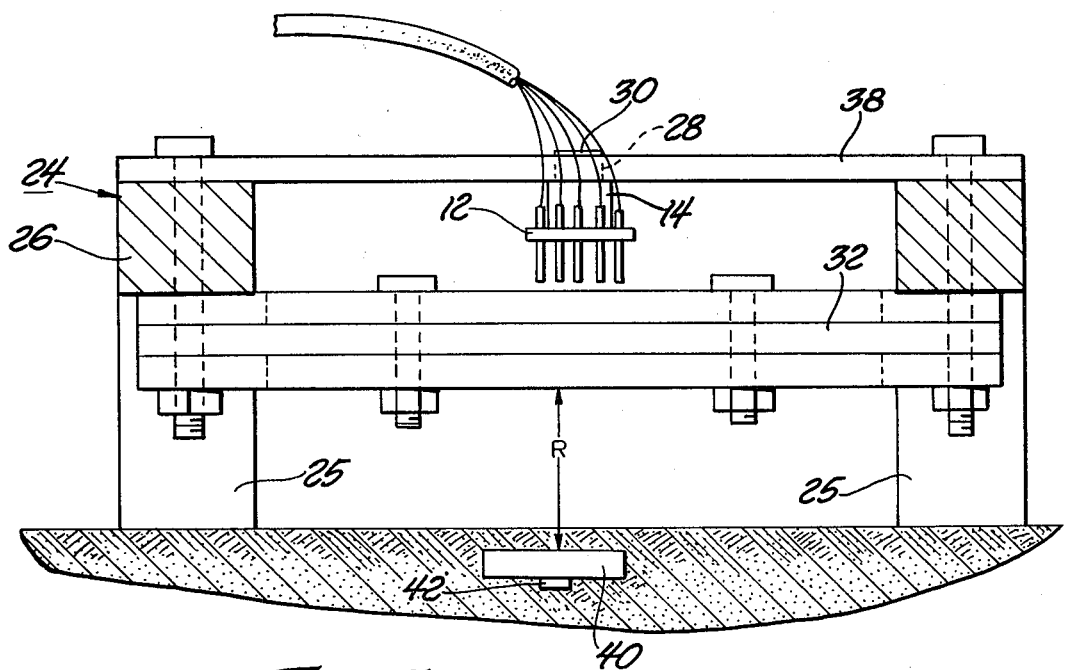
FIG. 5 is essentially an end elevational view of the test frame and transducer of FIG. 4, but viewed on line 5—5 of FIG. 4.

FIGS. 4 and 5 better disclose the testing apparatus which includes the framework generally designated 24, along with the main body part of the novel accelerometer transducer 10 in association with rigid plate 32 to be tested. The framework 24 as shown is of rectangular shape comprising laterally spaced, preferably parallel longitudinal beam members 26, 26 interconnected preferably by two parallel transverse end beams 36, 36 and a center cross beam 38. Transverse end beams 36, 36 and longitudinal side beams 26, 26 may be interconnected by various means such as by suitable nut and bolt assemblies 34. The bolts of the aforesaid assemblies generally extend completely through the test plate subassembly 32 and the longitudinal beams 26, 26 of the frame 24. The center transverse beam 38, which may be similarly bolted to the longitudinal members 26, 26 is preferably thicker than transverse end beams 36, 36, and has an opening 28 at its midpoint thereby enhancing the supportive mounting for upper portion 30 of the accelerometer transducer body 14. Beam frame members 26, 26 may be fabricated of composite laminates, if desired. The frame 24 is provided preferably with suitable legs 25, shown partially broken away in the FIGS. 5A through 5F sequence views. The legs 25 hold the test plate 32 in a fixed position relative to the ground or other base upon which the test is being conducted.

The entire frame assembly has a hold-down weight ratio of 28:1 test frame to test plate. The significance of this ratio, previously as explained, is to better simulate the same hold-down ratio which exists between the total weight of an armored vehicle and its undersurface or belly armor. In this manner, the testing apparatus may more accurately simulate actual armored vehicle characteristics and thereby provide correspondingly more realistic test performance data.

The accelerometer transducer 10, by its aforedescribed mounting in the center of transverse beam 38 via upper portion 30, or other suitable means, is held stationary in relation to the surface of test plate 32.

While the pins P are preferably held in a reasonably relatively fixed manner, their friction fit or other mounting is such that responsive to the high blast force, their respective plastic deformations are made initially and the contact times recorded, but the high residual force impact may be such as to impart some partial upward movement of various of the pins in their friction fit mounting in collar 12. Their relative displaced positions are evident in FIG. 3, by the comparison of pin end and wire connections 15, 18, compared to those shown in FIG. 1. If a further data-measuring calibrated rod is to be used by a slip fit through the center contemplated hole 16 of the transducer body 14, the lower end thereof will rest upon the plate to be tested, and the rod would extend perpendicularly upward. Measurement of its relative movement would be via the aforesaid calibrations measured at the top of portion 30, with help of a synchronized camera wired in the circuit. From the foregoing manner during actual testing, it is possible to measure exactly the distances between the ends of the respective pins and the surface of test plate 32. The data thus obtained is important in determining the change in velocity of the deforming surface as it strikes each pin. By a comparison of the postblast distances with the preblast distances of the various copper pins from the plate surface being tested ($\Delta x$) and a similar comparison of the times as seen in photographic prints of the oscilloscope tracings for each pin, it is possible to obtain an average velocity of the deforming surface of the test plate. That is, by subtracting the time between pin contacts, the incremental times ($\Delta t$) were obtained. The average velocity of the plate surface is computable from ($\Delta x/\Delta t$) and is assumed to occur at ($\Delta t/2$).

Figure 5A:
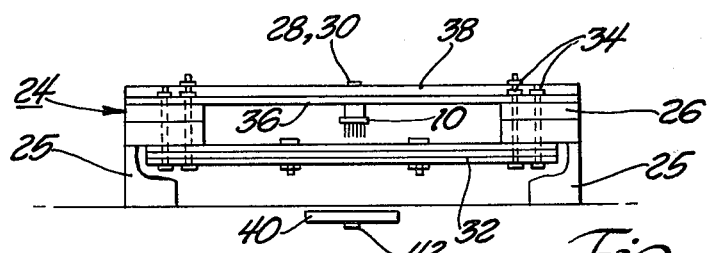
Figure 5B:
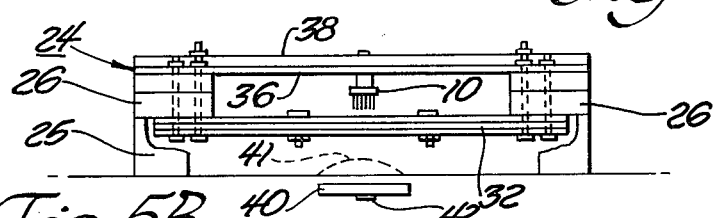
Figure 5C:
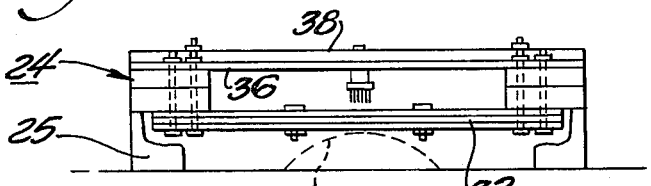
Figure 5D:
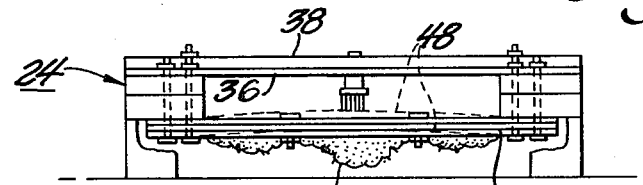
Figure 5E:
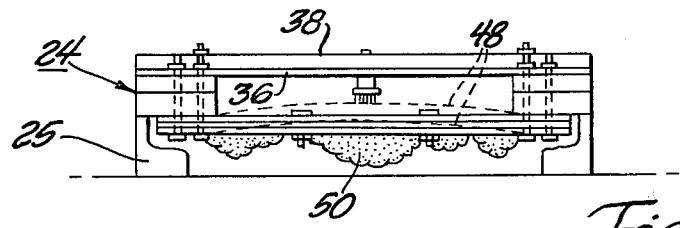
Figure 5F:
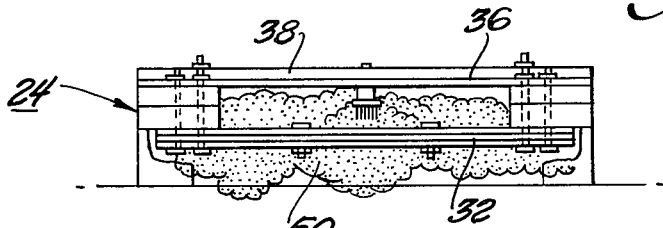

FIGS. 5A through 5F depict the sequence of events which occurs prior to and during blast force loading of the plate being tested. FIG. 5A shows an end elevational view of the testing apparatus with the noval blast accelerometer transducer (less the wire circuits) supported above a selected test plate member 32, and also above the explosive charge 40. FIG. 5B depicts the initial detonation force 41 of the charge 40 by an associated detonator 42. The weight of the scaled test explosive was 0.34 lb (154 g); the explosive geometry was 2.75 inch (7 cm) diameter by 1 inch thick (2.54 cm); the dry overlaid earth was 0.875 inch (2.2 cm) thick, and the distance R from the center of the explosive disc 40 to the botom of the test plate was 5.1 inch (1.3 cm). The detonator 42 is located preferably at the centerline and just below the explosive disc 40. As seen in FIG. 5C, the increasing detonation force 41 reaches the underside of the test plate 32 when the flash signal is at its peak flash point. FIG. 5D shows the explosive force 41 as it is transmitted to the test plate 32 with the resulting initial deformation of the test plate shown by the dotted line 48. FIG. 5E depicts the complete transfer of the explosive force to the test plate 32 and its increasing deformation 48. Note that the explosive force 41 has now degraded to explosion debris 50 and that deformation force 48 is reaching its maximum. Thereafter, as seen in FIG. 5F, the deformation force rapidly dissipates whereby the test plate returns to approximately its pretest configuration. Note that explosion debris 50 is now widely dispersed. Thus, via the series of events depicted in FIGS. 5A through 5F, the deforming test plate makes varying contact with various of the copper pins of the accelerometer transducer, and the pertinent time and other data are obtainable.

FIGS. 2 and 3 respectively show the novel accelerometer transducer 10 before and after receiving blast force loading by a deforming test plate. As seen in FIG. 3, after loading by the test plate, the copper pins are in various stages of deformity from the impact. By measuring the deformities caused by the force loading, the instantaneous particle velocity can be computed. This is done by measuring the diameter of the pin end which is to be impacted by the deforming plate before the testing is done and then again measuring it after the test is completed. Due to inherent plastic radial strain or deformation characteristics known to be present in pure annealed metals, the end of the sharply impacted pin will have a greater diameter than that of the nonimpacted pretest pin. Since the plastic radial strain of various pure metals is known and obtainable from prior research test data/articles, it is possible to derive the instantaneous particle velocity of the metallic plate as it strikes the copper (or other named metallic) pin probes discussed further hereinafter.

In this latter regard, instantaneous velocity measurements at the time of pin contact with the test plate are obtainable by utilizing the stress-intensity deformations of a (known) rod relationship as the basis for a velocity-measuring transducer. Prior engineering studies ("The Permanent Strain in a Uniform Bar Due to Longitudinal Impact," an article by M. P. White and L. Griffis, appearing in the *Journal of Applied Physics,* S. A., December 1947, pp. 337–343) shown that if the longitudinal plastic strain of a copper pin (of given size) is known, then it is possible to predict the instantaneous velocity of contact by means of the graph/table of FIG. 8, given the tensile stress-strain relationship for annealed copper, as set forth in FIG. 9. The same authors in another article "The Propagation of Plasticity in Uniaxial Compression," in Volume 15, September 1948, pp. 256–260 of the same Journal, also show that the compression stress-strain relationship is identical to that in tension up to plastic strains of about 40 percent. In other studies ("The Propagation of Plastic Deformation in Solids," by T. Von Karman and P. Deevey, published in the Volume 21 October 1950 *Journal of Applied Physics,* pp. 987–994) it was shown that the plastic strain for a copper wire remains constant for a significant length from the end of impact. The latter event occurs prior to the buckling shown in FIGS. 3 and 6D. It was found also that at the end of the constant plastic strain region a significant abrupt lessening of the plastic strain is observed from experiment and confirmed by theory. The diameter of the end region for each of the copper pins (usually eight per test) was measured and plotted on graphs (of the type shown in FIGS. 8 and 9) in conjunction with the latter-mentioned report work. The pin probes used when measured after plate contact ranged in diameter from about 0.066 to 0.086 inch, with original pin diameter being 0.066 inch.

This latter study reportedly assumed that the plastic deformation of the end of the copper pin is characterized by an incompressible volume deformation process. The radial plastic strain $\epsilon_r$ computed as $\epsilon_r = (d - 0.066)/0.066$, where d is the pin diameter of impact end region thereof. The original pin diameter was 0.066 inches. The longitudinal strain $\epsilon_l$ is then obtained from the incompressible volume assumption, $$\epsilon_l = (l + \epsilon_r)^{-2} - 1$$

In this manner it is found that $\epsilon_1$ ranges from $-0.246$ for plate P7 to $-0.411$ for plate P13, with respect to a plurality of 14 test plates designated P1–P14 inclusive. Since the stress-strain curve for pure copper is the same up to 40 percent strain in either compression or tension, one can use FIGS. 8 and 9 to obtain the impact velocity and force transmitted to the copper pins at the instant of plate impact. The following Table A lists these impact velocities for each test and for each of the eight pins used in each test. These velocity profiles are shown in the order from the least violent (plate P14) to the most violent (plates P., P11). Table B similarly shows the profile of the initial impact force on the various pins P.

TABLE A

Plate velocity obtained from plastic deformation of copper pins

| Plate No. | Plate displacement, CM | | | | | | | |
|---|---|---|---|---|---|---|---|---|
| | 0.025 | 0.254 | 0.508 | 0.762 | 1.016 | 1.270 | 1.905 | 2.540 |
| P14 | 81 | 77 | 62 | 62 | 53 | 27 | 3 | 3 |
| P7 | 81 | 77 | 73 | 53 | 53 | 27 | 3 | 3 |
| P9 | 86 | 81 | 73 | 63 | 38 | 27 | 3 | — |
| P10 | 92 | 81 | 68 | 53 | 38 | 38 | 27 | — |
| P15 | 90 | 81 | 77 | 62 | 45 | 38 | 3 | 3 |
| P12 | 90 | 81 | 77 | 73 | 62 | 45 | 27 | 3 |
| P5 | 86 | 81 | 68 | 68 | 53 | 45 | 38 | 27 |
| P3 | 90 | 90 | 86 | 73 | 53 | 38 | 38 | 27 |
| P8 | 86 | 86 | 73 | 73 | 68 | 53 | 38 | 27 |
| P6 | 86 | 81 | 77 | 73 | 73 | 68 | 68 | 68 |
| P4 | 97 | 90 | 86 | 77 | 73 | 45 | 27 | — |
| P2 | 100 | 100 | 97 | 90 | 86 | 77 | — | 27 |
| P13 | 113 | 111 | 104 | 81 | 77 | 62 | 27 | 3 |
| P1 | 107 | 100 | 97 | 92 | 92 | 92 | — | 62 |
| P11 | 107 | 104 | 100 | 97 | 68 | 62 | 38 | 27 |

TABLE B

Forces transmitted between plate and copper pin (pounds)

| Plate No. | Plate displacement, CM | | | | | | | |
|---|---|---|---|---|---|---|---|---|
| | 0.025 | 0.254 | 0.508 | 0.762 | 1.016 | 1.270 | 1.905 | 2.540 |
| P14 | 128 | 128 | 110 | 110 | 100 | 61 | 30 | 30 |
| P7 | 128 | 128 | 122 | 100 | 100 | 61 | 30 | 30 |
| P9 | 137 | 128 | 122 | 116 | 80 | 61 | 30 | — |
| P10 | 142 | 128 | 116 | 100 | 80 | 80 | 61 | — |
| P15 | 139 | 128 | 126 | 110 | 91 | 80 | 30 | 30 |
| P12 | 139 | 128 | 128 | 122 | 110 | 91 | 61 | 30 |
| P5 | 139 | 128 | 116 | 116 | 100 | 91 | 80 | 61 |
| P3 | 139 | 139 | 139 | 122 | 100 | 80 | 80 | 61 |
| P8 | 139 | 139 | 122 | 122 | 116 | 100 | 80 | 61 |
| P6 | 139 | 128 | 126 | 122 | 122 | 116 | 116 | 116 |
| P4 | 145 | 139 | 139 | 126 | 122 | 91 | 61 | 61 |
| P2 | 149 | 149 | 145 | 139 | 137 | 126 | — | 61 |
| P13 | 161 | 159 | 153 | 128 | 128 | 110 | 61 | 30 |
| P1 | 156 | 149 | 145 | 142 | 142 | 142 | — | 110 |
| P11 | 156 | 153 | 149 | 145 | 116 | 110 | 80 | 61 |

Figure 6A:
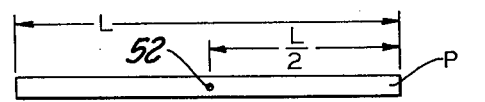
FIGS. 6A through 6E represent the progressive stages of a single copper pin probe deformation, commencing prior to any plate impact and ending with the postblast net deformation remaining in the end of the pin at the time of the pin and test plate separation.
Figure 6B:
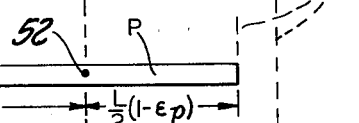

The deformity of the pins is better shown illustratively in FIGS. 6A through 6E, wherein a single exemplary copper pin P is shown in progressive stages prior to and during the blast loading impact by the deforming test plate. The first part, FIG. 6A, depicts a nondeformed copper pin P prior to impact loading by test plate 32. The pin's center of gravity is designated 52. The pin is of length L, and from the center of gravity 52 to either end of the pin is ½L. FIG. 6B depicts the initial onset of the aforementioned plastic strain imparted to one end of the pin by the deforming plate as shown by the broken line 32. As the pin is progressively compressed, its length decreases while its diameter increases on that end portion which is in contact with the deforming plate surface. Note that in FIG. 6B, the center of gravity 52 remains unchanged at this early stage of impact.

Figure 6C:
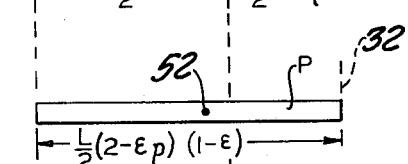
Figure 6D:
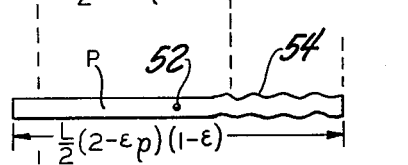
Figure 6E:
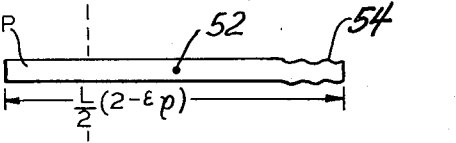

As the compressive elastic strain is being partially absorbed and stored in the pin as seen in FIG. 6C, the center of gravity 52 begins to shift away from the deforming plate surface so as to remain in the center of the mass of the compressed pin. As the pin continues to be compressed, its length decreases but its diametrical thickness increases in the impacted end portion while its mass remains constant. This is representative of the so-called plastic strain mentioned above. Thus, the center of gravity shifts. As more compressive elastic strain energy is stored in the pin, the pin starts to exhibit instabilities or bending 54 as seen in FIG. 6D. These instabilities or bends are the result of the inability of the pin to absorb any more energy or to compress any further. At that point, following maximum test plate deflection and the latter's beginning separation back away from the pin, the length of the pin begins to increase as the instabilities allow some of the stored compressive elastic strain to be released. By the time the pin and test plate have fully separated, as represented in FIG. 6E, all the remaining stored compressive elastic strain energy of the pin is released. Thus, the compressed length of the pin again slightly increases, but it does not return to its original length or diameter dimensions. Rather, there remains a partial deformation 54 of the end of the pin and a slight increase in the thickness thereof, thereby causing it to be somewhat shorter than its original length. By measuring the end thickness before and after the deformation process, the instant particle velocity for each pin can be obtained as discussed hereinabove.

The average acceleration of the plate can be obtained by dividing the change in velocity ($\Delta v$) by the change in time ($\Delta t$), as per the following example:

$$\frac{\Delta v}{\Delta t} = \frac{v_1 - v_2}{t_1 - t_2}$$

Where
$v_1$ is the instantaneous velocity of pin 1
$v_2$ is the instantaneous velocity of pin 2
$t_1$ is initial time of pin-to-plate contact of pin 1
$t_2$ is initial time of pin-to-plate contact of pin 2

The structure and operation are deemed to be clearly disclosed from the foregoing description. The attendant novel method is briefly summarized as follows: At least two pure copper annealed pins are located a short distance apart in a holder which is attached to support a structure and closely adjacent a rigid test plate also rigidly held by the support structure, with the plate disposed over an explosive charge of predetermined size. The pins are of different lengths or positioned to project at different lengths from the pin's support member, so that they are essentially perpendicular to and at slightly different distances from the test plate. Upon test plate deformation and its impact on the copper pins, the pins undergo different extents of plastic deformation near their struck ends. The plastic stress waves and/or physical change phenomena applicable to various pure metal wires/rods are well known to engineers and others skilled in the plastic theory and plastic stress wave art. The change in time ($\Delta t$) between the contact of the two pins with the plate may be recorded by any number of methods, in this case by an oscilloscope voltmeter. By measuring aforenoted time differences and the thickness of the ends of the pins struck by the deforming plate at any time after the tests, engineers experienced in this art can compute the instant particle velocity for each pin end, as well as the aforesaid average acceleration.

From the foregoing detailed descriptions, it is apparent that a novel accelerometer transducer has been evolved which satisfies the objectives and advantages attendant such invention, including a novel testing system and novel manner of determining average acceleration of a blast deformed plate to facilitate improving designs of armor steel plate, more preferably of the composite type.

It is also understood that for certain circumstances where only a velocity value is needed, by utilizing only a single pin transducer of the present type, in conjunction with the aforementioned type table data (such as given in FIGS. 8 and 9 or the like), a further unique and novel advance is evolved in the field of velocity transducers. By use of this further single pin system, there is no need to measure distance or time as is required with other such velocity transducers of which I am aware.

Relevant portions of each of the foregoing referred to publications are hereby incorporated by reference for further clarifying and supporting this disclosure, as may be desired or needed by those skilled or unskilled in the art.

I wish it to be understood that I do not desire to be limited to the exact details of construction shown and described for obvious modifications will occur to a person skilled in the art. Accordingly, reference should be made to the appended claims for a definition of the scope of the claimed subject matter herein.

I claim:

1. A system embodying novel, motion-sensing accelerometer transducer means for measuring exceptionally high force levels in the domain of from about 1,000,000 to 10,000,000 Gs and also for facilitating measuring structural deformation and average velocity of such deformation of normally high strength structural panel means having planar surfaces, such as steel armor plate and the like as used on military tanks and other armored vehicles which are subject to close-by detonation of high energy explosive charges, such as land mines and the like, said system comprising in combination:
   a. selectively closeable and openable, principal electrical circuit means for measuring and obtaining evaluating data for computing desired measurements, said principal circuit means including wire conductor cable means with means for selectively connecting said cable means with a source of d.c. electrical current;
   b. said circuit means also including conductor cable terminal means adaptable to be connected to said structural means as a negative ground portion of said circuit;
   c. novel, motion-sensing accelerometer transducer means having body means, a plurality of metallic pin-like contact probes supported by said body means, said probes having respective first ends projecting freely from said body means so that said free ends are closely adjacent but at relatively slightly different distances from said planar surface of a structure whose deformation is to be sensed and measured, said first-end-spacings from said surface being such as to have at least two of said probe ends potentially contactable by the deforming surface;
   d. means for supporting said transducer means in a position closely adjacent the structural planar surface to be subjected to deformation;
   e. said principal electrical circuit means further including a plurality of electrical probe conductor wires each connected at one end respectively with a separate portion of said respective probes which separate portion is remote from said first free ends thereof, said probe conductor wires forming plural in-parallel subcircuits for each probe and respectively connected in said principal circuit means to be potentially activated by said electrical power source and plate-to-pin contact closure of the subcircuit;
   f. each of said in-parallel subcircuits including a resistance capacitor and fast-response electrical data measuring and recording means connected in series between said probe and said principal circuit conductor cable ahead of said means for selectively connecting it with the power source;
   g. whereby at least two of said in-parallel subcircuits are adapted to be closed when a said deformable structural surface is blast force deformed so as to make at least brief said electrical plate-to-pin contact with said corresponding at least two probes, and whereby the respective resistance capacitor is discharged to thereby instantaneously generate signal data for reading by display on said data measuring and recording means.

2. A system as defined in claim 1, wherein said resistance capacitor of each subcircuit is of the single discharge type, and said fast-response electrical data measuring and recording means in each subcircuit is of an oscilloscope voltmeter type instrument capable of generating time sweep signal data in for visual display in a readout window of said instrument/oscilloscope.

3. A system as defined in claim 2, wherein said fast-response electrical data-recording means further includes high speed camera means focused upon said readout window, and having means for electrically connecting and activating said camera means into the respective subcircuits so as to record on camera film a series of picture frames of the respective instrument/oscilloscope-produced time sweep signal data of at least the instant of plate structure-to-pin contact.

4. A system as defined in claim 1, wherein said probes are fabricated of deformable, essentially pure metal wire, and wherein said respective portions of said probes which are remote from said respective linear free end portions are the opposite terminal ends which constitute a second set of probe ends adjacent said transducer body means, said second set of probe ends adaptable for quick electrical connect-disconnect with corresponding terminal connecting means of said in-parallel subcircuit probe conductor wires.

5. A subcombination of a motion-sensing accelerometer transducer for use with a structure having a normally rigid high-strength planar surface capable of being blast deformed under certain conditions, and which surface is to be motion-sensed collectively by this transducer and other data-recording instruments within a system for measuring exceptionally high force levels in the domain of from about 1,000,000 to 10,000,000 Gs as may be generated by detonation of explosive blasts or charges such as land mines and the like, and which resultant forces are capable of imparting at least temporary structural deformation to at least some close-by portions of said normally rigid, high strength structural surface, such as armor steel plate and the like, said subcombination accelerometer transducer comprising:
   a. a plurality of at least two wire or pin-like contact probes of relatively short length, said probes terminating in free ends coonstituting a first set of probe free ends, each probe:
      (1) being potentially deformable in at least its free end portion thereof, upon impact by an adjacent structure when subjected to an aforesaid high force level;
      (2) having at least a substantial nondeformed linear end portion of uniform diameter, and
      (3) having a portion remote from said linear free end portion adaptable for electrical connection with wire conductor subcircuit means used in conjunction with said data-recording instruments;
   b. a support member for supporting said probes in a normally relatively fixed manner whereby said first set of free ends of said probes projects freely beyond said support member with at least one of said contact probe free ends projecting slightly beyond another thereof, and
   c. said contact probes being of a normally initially rigid material with excellent electrical conducting properties capable of instantaneously conducting an electrical current therethrough when deployed in and as part of an electrical circuit in a system connectable with an electrical power source.

6. The accelerometer transducer subcombination of claim 5, wherein said plurality of contact probes number between 6 and 8, and said first set of free ends of the probes project with their linear portions generally parallel, and with their free ends respectively terminating at slightly different relative lengths, so that when the accelerometer transducer is placed adjacent a planar-surfaced structure whose motion is to be sensed, it is disposed with said parallel linear portions of said probes generally perpendicular to said planar surface and so that said respective contact ends of said first set respectively are at slightly different relative distances from said planar surface.

7. The subcombination of claim 5 or 6, wherein said support member includes a planar portion through which said probes are mounted so as to be electrically insulated therefrom.

8. The subcombination of claim 5 or 6, wherein said support member includes a medial body portion having a laterally projecting generally planar flange portion through which said probes are adjustably mounted in a manner so as to be electrically insulated therefrom.

9. The subcombination of claim 5 or 6, wherein said probes are made of the same type relatively soft, malleable metal having excellent electrical current conducting properties, and selected from a group of metals including copper, silver, gold, lead and aluminum.

10. The subcombination of claim 5, wherein said probes are all similarly made from the same type pure annealed metal wire selected from a group of metal wires including copper, silver, gold, lead and aluminum.

11. The subcombination of claim 5 or 10, wherein said probes have an initial cross-sectional thickness of about 0.066 inch for at least a major part of the length of said first set of free ends projecting from said support member.

12. The subcombination of claim 5 or 6, wherein said plurality of pin probes are disposed in a generally circular pattern extending through a support flange projecting laterally from said support member, and said probes and support flange being electrically insulated from one another.

13. A method for sensing/determining motion and/or at least temporary deformation and for determining attendant instantaneous velocity and acceleration of a normally high strength generally planar structural surface when subjected to high energy explosive charge blast loading, said method comprising the steps of:
   a. positioning said structural surface in a manner to provide relatively rigid orientation in predetermined close proximity to an explosive charge and oriented with a major plane thereof generally perpendicular to the expected blast force;
   b. mounting an accelerometer transducer of the multiple deformable metal pin-probe type, such as defined in claim 5, in a rigid manner adjacent said surface, so that at least two of the deformable pins have free ends spaced relatively close to but at slightly different distances from said surface to undergo blast loading;
   c. connecting said multiple pin-probes respectively in parallel electrical subcircuits each having a series connected resistance capacitor and fast response data generating, timing and data displaying means adapted to potentially display on each such means at least one time sweep signal spike generated responsive to progressive closure of said subcircuits when the latter are connected in a principal circuit means to d.c. power source and to a ground station on said plate surface, said respective subcircuits being potentially closeable attendant blast-induced plate deformation contact with each pin-probe,
   d. detonating the explosive charge adjacent said plate surface and thereby blast-imparting at least some temporary deformation thereto sufficient to make at least brief physical and electrical contact with at least two of said multiple probes,
   e. measuring and recording the difference in time ($\Delta t$) between progressive plate-to-pin probe contacts by comparing records of the respective fast response data-displaying readings,
   f. comparing preblast, nondeformed diameters and post-blast, plate-impacted-deformed diameters of the free ends of the pin probes, also of the same relative distances between said plate and said pin free ends ($\Delta x$), and consulting engineering graphs and tables showing computed plastic deformation and end strain data for known types of metals which include the type of metal pin probe used, to obtain impact velocity and to compute average velocity of the plate deformation from a computation of ($\Delta x/\Delta t$).

14. The method of claim 13, wherein said fast response, data-generating, timing and data-displaying means is an oscilloscope voltmeter type instrument.

15. The method of claim 13, further including using probes of pure annealed metal wire from a group of metals comprising copper, silver, gold, lead and aluminum.

16. The method of claim 13, further including using between six and eight probes of pure annealed metal wire with the probes arranged in a generally circular manner and project with free probe ends disposed at slightly relatively different lengths from one another.

17. The method of claim 13, further including computing average acceleration of the deformable plate, which average acceleration is represented by the formula:

$$\frac{\Delta v}{\Delta t} = \frac{v_1 - v_2}{t_1 - t_2}$$

where $v_1$ is the instantaneous velocity of a given first pin (pin 1),
$v_2$ is the instantaneous velocity of a given second pin (pin 2),
$t_1$ is initial time of pin-to-plate contact of pin 1,
$t_2$ is final time of pin-to-plate contact of pin 2.

* * * * *